United States Patent
Yanguas-Gil et al.

(10) Patent No.: US 9,727,672 B2
(45) Date of Patent: Aug. 8, 2017

(54) FAST METHOD FOR REACTOR AND FEATURE SCALE COUPLING IN ALD AND CVD

(71) Applicant: UChicago Argonne, LLC, Chicago, IL (US)

(72) Inventors: Angel Yanguas-Gil, Northbrook, IL (US); Jeffrey W. Elam, Elmhurst, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 346 days.

(21) Appl. No.: 14/633,025

(22) Filed: Feb. 26, 2015

(65) Prior Publication Data
US 2016/0253441 A1    Sep. 1, 2016

(51) Int. Cl.
G06F 17/50    (2006.01)

(52) U.S. Cl.
CPC ................... G06F 17/5009 (2013.01)

(58) Field of Classification Search
USPC .................... 703/2, 18; 700/121; 438/706
See application file for complete search history.

(56) References Cited

U.S. PATENT DOCUMENTS

| | | | | |
|---|---|---|---|---|
| 6,577,915 B1* | 6/2003 | Cooperberg | ...... | H01J 37/32935 438/9 |
| 7,139,632 B2* | 11/2006 | Cooperberg | .......... | H01J 37/321 156/345.24 |
| 8,230,807 B2* | 7/2012 | Alcott | .................. | B05D 1/60 118/715 |
| 8,548,787 B2* | 10/2013 | Tamaoki | ................ | C23C 14/54 438/706 |
| 2005/0278057 A1* | 12/2005 | Cooperberg | .......... | H01J 37/321 700/121 |
| 2007/0118341 A1* | 5/2007 | Tamaoki | ................ | C23C 14/54 703/2 |
| 2008/0038484 A1* | 2/2008 | Alcott | .................. | B05D 1/60 427/579 |

(Continued)

OTHER PUBLICATIONS

Cale, et al., "Free molecular transport and deposition in long rectangular trenches," Journal of Applied Physics, vol. 68, No. 7, Oct. 1, 1990, 9 pages.

(Continued)

*Primary Examiner* — Thai Phan
(74) *Attorney, Agent, or Firm* — Foley & Lardner LLP

(57) ABSTRACT

Transport and surface chemistry of certain deposition techniques is modeled. Methods provide a model of the transport inside nanostructures as a single-particle discrete Markov chain process. This approach decouples the complexity of the surface chemistry from the transport model, thus allowing its application under general surface chemistry conditions, including atomic layer deposition (ALD) and chemical vapor deposition (CVD). Methods provide for determination of determine statistical information of the trajectory of individual molecules, such as the average interaction time or the number of wall collisions for molecules entering the nanostructures as well as to track the relative contributions to thin-film growth of different independent reaction pathways at each point of the feature.

17 Claims, 15 Drawing Sheets

(56) References Cited

U.S. PATENT DOCUMENTS

2010/0084276 A1* 4/2010 Lindsay ............... C12Q 1/6869
205/93

OTHER PUBLICATIONS

Dendooven, et al., "Modeling the Conformality of Atomic Layer Deposition: The Effect of Sticking Probability," Journal of the Electrochemical Society, Feb. 2009, vol. 156, No. 4, 5 pages.

Islamraja, et al., "A 3-dimensional model for low-pressure chemical-vapor-deposition step coverage in trenches and circular vias," Journal of Applied Physics, vol. 70, No. 11, Dec. 1, 1991, 5 pages.

Kim, et al., "Applicability of Step-Coverage Modeling in TiO2 Thin Films in Atomic Layer Deposition," Journal of the Electrochemical Society, Oct. 2007, vol. 154, No. 12, 6 pages.

Knoops, et al., "Surface Loss in Ozone-Based Atomic Layer Deposition Processes," Chemistry of Materials, Apr. 2011, vol. 23, 7 pages.

Knudsen, et al., "Knudsen self- and Fickian diffusion in rough nanoporous media," Journal of Chemical Physics vol. 119, No. 5, Aug. 2003, 12 pages.

Kukli, et al., "Influence of atomic layer deposition parameters on the phase content of Ta2O5 films," Journal of Crystal Growth, May 2000, vol. 212, 10 pages.

Raupp, et al., "Step Coverage Prediction in Low-Pressure Chemical Vapor Deposition," Chemistry of Materials, Mar. 1989, vol. 1, No. 2, 8 pages.

Shimogaki, et al., "The Reactivity and Molecular Size of Film Precursors During Chemical Vapor Deposition of WSix," Journal de Physique IV, Sep. 1991, C2, 8 pages.

Tisone, et al., "Step coverage in the vacuum deposition of thin metal films," Journal of Vacuum Science and Technology, vol. 11, No. 1, Jan./Feb. 1974, 6 pages.

Yanguas-Gil, et al., "Highly conformal film growth by chemical vapor deposition. II. Conformality enhancement through growth inhibition," Journal of Vacuum Science and Technology, vol. 27, No. 5, Sep./Oct. 2009, 6 pages.

Yanguas-Gil, et al., "Self-Limited Reaction-Diffusion in Nanostructured Substrates: Surface Coverage Dynamics and Analytic Approximations to ALD Saturation Times," Chemical Vapor Deposition, Mar. 2012, vol. 18, 7 pages.

Yanguas-Gill et al., A Markov chain approach to simulate Atomic Layer Deposition chemistry and transport inside nanostructured substrates, Thero Chem ACC (2013) 133, Feb. 26, 2014, 13 pages.

* cited by examiner

FAST METHOD FOR REACTOR AND FEATURE SCALE COUPLING IN ALD AND CVD

STATEMENT OF GOVERNMENT INTEREST

The United States Government has rights in the invention described herein pursuant to Contract No. DE-AC02-06CH11357 between the United States Department of Energy and UChicago Argonne, LLC, as operator of Argonne National Laboratory.

FIELD OF THE INVENTION

The present invention generally relates to material deposition techniques and models for same.

BACKGROUND OF THE INVENTION

The coating of nanostructured features with homogeneous films or particles is a technological need in application fields ranging from semiconductor manufacturing to nanostructured photovoltaics, energy storage and catalysis. This problem has been studied previously in the context of different thin-film deposition techniques, including physical vapor deposition, chemical vapor deposition (CVD) (both thermal and plasma enhanced) and, more recently, atomic layer deposition (ALD).

In order to develop new processes and materials with the desired properties or to design better equipment is to understand how the experimental variables affect the coating process. To achieve this, computational models of varying degrees of complexity have been applied to the simulation of the coating process, and they are part of the prior art. In their more complete version, these models consider the transport and reaction of gases in a reactor, reacting cell or in general in a region of the space. In the most general processes, different species in the liquid or gaseous phase react with each other both in the same phase, on the surface of the material or inside the material itself. The growing material generally and/or its surface is also an active component of the overall reaction process.

A similar approach, but with potentially different models, can be applied to simulate the reaction and transport of gaseous or liquid species in nanostructured materials.

In one implementation, nanostructured materials are materials whose features are characterized by a size which is at least three orders of magnitude smaller than that of the reactor-scale simulation size in at least one dimension. These may include surfaces with microscopic features, porous particles, sculptural films, colloidal films or films composed of nanoparticles, nanotubes, fiber bundles, polymer and block-copolymer films, and textiles or surfaces with microelectromechanical devices or MEMS. The key aspect of these materials is that, due to the significant difference in length scale between reactor scale and the feature scale, a single model comprising both reactor and feature scale would be computationally very expensive, since it would force the reactor to be simulated with a degree of detail far exceeding that required to capture the phenomenology of the reactive transport outside the nanostructured substrate.

For these cases, the prior art has approached this problem by applying multiscale model approaches to the simulation of these systems: the reactor-scale model is solved at a length scale relevant for that problem, and a separate model takes place of the transport inside the nanostructured material, and those two models are linked in such a way that only the relevant information is passed between the two models to be able to solve the transport and reaction of species at both separate length scales simultaneously.

The state of the art approach to solve this problem can be summarized as folios: at a reactor scale, the simulation domain is divided in a series of interconnected regions. At any given iteration of the process, for every region facing the nanostructure substrate, the specific model for the nanostructure substrate is then applied and the transport inside the nanostructured material is solved. This means that, if it takes $N_t$ iterations to solve the model to its completion (either because it converges to a stable solution or because, in a time-dependent simulation it reaches to the target final time) and there are $N_s$ regions facing the nanostructured material, the nanostructured material model needs to be solved $N_t \times N_s$ times. This means that if the time $D_t$ is very high, the repetitive application of the feature scale model becomes extremely time consuming part of the solution process.

One important feature of the prior art is that the state of the nanostructured material is constantly stored and updated in each iteration. For instance, the reactive transport in the nanostructured material can solved by applying a discretization algorithm to the nanostructured material in a similar way as described above for the reactor scale. The state of the system therefore is determined by the value of the relevant variables on each of the N discretized regions of the nanostructure. The state must be stored and updated for each of the Ns elements interfacing the nanostructured material at the reactor scale.

Consequently, the application of multiscale models to the simulation of the coating of nanostructured materials requires substantially more computational power and memory that the simulation on the flat surfaces. It also relies on two models that are intimately linked within the simulation, meaning that models that can solve the reactor scale transport in absence of nanostructured materials cannot be updated to incorporate the nanostructured materials without substantial rework. This makes it almost impossible to apply an existing reactor-scale model for the case of closed-source software.

The application domain of the current invention pertains to the synthesis of materials as thin films using a plurality of methods, including sputtering, evaporation, chemical vapor deposition, and atomic layer deposition. Of these methods, Atomic Layer Deposition is of particular relevance due to its time-dependent nature, which makes the application of simulations to model the growth process much more computationally expensive. Due to its self-limited surface chemistry, ALD is intrinsically conformal and therefore it can achieve uniform coatings in high aspect ratio features and large-area substrates. This attribute makes ALD intrinsically scalable, facilitating the transition from lab-scale research to prototype. However, beyond the prototype scale, the economic aspects of a process, such as throughput and materials utilization, become crucial for advancing the process to manufacturing. Moreover, small departures from ideal self-limited ALD surface chemistry, which may be irrelevant at a small length scales, can greatly condition the process at large scale. Therefore, advances in the way models are applied to the simulation of Atomic Layer Deposition can facilitate the scale up process and the design of more efficient tools, and impact fields as diverse as semiconductor processing, energy storage, solar energy, and catalysis.

From a theoretical perspective, one important advantage of ALD compared with CVD and plasma enhanced CVD (PECVD) is the lack of homogeneous processes: This greatly simplifies the task of developing general models applicable to a wide range of systems, especially when simple surface kinetic models are good approximations for the self-limited surface kinetics. For instance, in a previous work, the following expression was derived to predict the exposure required to coat a nanostructured feature under the common first-order irreversible Langmuir kinetics:

$$pt_c = \frac{\sqrt{2\pi mkT}}{s_0} \frac{3}{2}(AR)^2 \left(1 - \frac{2\log(1-c_0)}{3\beta(AR)^2}\right) \quad 1)$$

where AR is the aspect ratio of the feature; $\beta$ is the bare reaction probability of the first-order irreversible Langmuir kinetic model for the ALD chemistry; $s_0$ is the average area of a surface site; m is the precursor mass; k is the Boltzmann constant; p is the precursor vapor pressure; $t_c$ is the exposure time; $c_0$ is the normalized coverage; and T is the temperature. While similar expressions can be obtained for the single-source precursor low-pressure CVD, these conditions represent only a small subset of the parameter space for CVD. In contrast, Eq. 1 applies to any ALD process that can be represented by this simple, ideal surface kinetics.

However, the simple first-order Langmuir kinetics that can be represented by Eq. 1 are sometimes insufficient to capture the complexities of the real-world ALD surface chemistry necessary for useful applications. Well-known instances include non self-limited surface recombination of species in radical and plasma enhanced ALD, ozone recombination, "parasitic" CVD, re-adsorption of gaseous products, and etching. Even the prototypical example for $Al_2O_3$ ALD using trimethyl aluminum and $H_2O$ shows nonideal behavior for the $H_2O$ saturation. In fact, it is safe to say that virtually all ALD processes are non-ideal in the limit of very large precursor exposures. Therefore, while the use of first-order kinetics (and with them Eq. 1) is useful to understand the universality of growth under ideal self-limited conditions, it fails to reproduce the nuances of some technologically relevant ALD processes. This problem is further amplified in the presence of nanostructured materials.

Thus, there is a need for systems and method to model real-world deposition processes on nanostructured materials that can accommodate complex precursor-surface interactions and that can be solved fast enough to allow their application to the optimization of a process, a reactor design, and the final product.

SUMMARY OF THE INVENTION

One embodiment of the invention relates to a method for modeling to model reaction and transport of gases and liquid. The method comprises: identifying a set of tracking variables that completely define the state of the nanostructured material; identifying a set of output variables that completely define the impact of the nanostructured substrate at the reactor scale; computing, via a processor of a computer, the set of output variables as a function of the set of tracking variables to generate a functional relationship between the set of tracking variables and the set of output variables; storing the functional relationship between the tracking and the output variables both as a data structure in a memory of the computer; solving the reactive transport at a reactor scale of the reacting species and the tracking variables using an iterative method; and determining, via the processor, the value of the output variables from the tracking variables using the functional relationship between them stored in the memory for every discretized region of the reactor-scale model interacting with the nanostructured material and for all iteration steps.

Another implementation relates to a method for simulating reactor-scale ALD. The method comprises generating a look-up table for feature-scale values; applying a feature-scale model having a plurality of time-steps; for each of the plurality of time steps, identifying a plurality of surface element; for each plurality of surface elements corresponding to each of the plurality of time steps, determining a total precursor exposure and querying the look-up table based upon the determined total precursor exposure to determine a reaction probability; and applying the reaction probability at the reactor-scale.

Another implementation relates to a computer implemented system for simulating reactor-scale ALD. The system comprises a processor and non-transitory computer-readable memory having instructions thereon. The instructions being for determining nanostructures for the thin film deposition; modeling transport of a reacting molecule in the thin film deposition as a Markov chain process; determining a probability that a reacting molecule adsorbs; and applying the probably to a reactor-scale to simulate a thin film deposition on a reactor scale.

Another implementation relates to a method to allow the concurrent solution of the coating of nanostructured materials. The method consisting of: solving a feature-scale model to determine look-up tables for the relevant tracking and output variables for the nanostructured material; storing the results in a database for future retrieval; and concurrently solving the reactor-scale model for a multiplicity of conditions and reactor configurations.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION OF THE PREFERRED EMBODIMENTS

Figure 1:
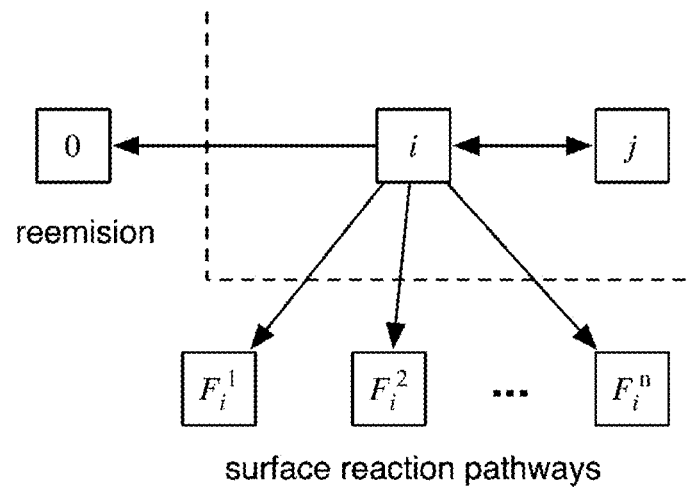
FIG. 1 illustrates a scheme of the allowed transition between different states of the Markov Chain model.

The present invention provides a new way of applying multiscale simulations to model the reactive transport of species in presence of nanostructured surfaces, optimize the design of said process, and of the design of the physical system in which said process takes place.

One of the embodiments of the invention relates to the application of multiscale models to the simulation of materials. This embodiment comprises the following components: a reactor-scale model, a feature-scale model, a set of tracking variables, and a set of output variables. The components are defined as follows.

The reactor scale model refers to any method used to simulate the reactive transport of gaseous species at a reactor scale. It includes computational fluid dynamic models, dynamic Monte Carlo simulations, ballistic models, lattice Boltzmann methods and other methods specified in the prior art.

The feature scale model refers to any method used to simulate the reactive transport of gaseous species inside nanostructured materials. It includes computational fluid dynamic models, continuum descriptions based on Knudsen diffusion, ballistic models, Monte Carlo methods, lattice Boltzmann methods, cellular automata and other methods specified in the prior art, as well as the Markov Chain method described above.

The set of tracking variables refers to a small set of variables, typically 1-10, that completely determine the state of the nanostructured material.

The set of output variables refer to the key variables that the reactor-scale model requires in order to account for the presence of nanostructured material in the reactor. These variables are supplied by the feature-scale model.

A key property of this embodiment is that the reactor and feature scale models are not solved concurrently. Instead, the feature model is applied first to the problem, and the result can be then supplied to a multiplicity of reactor-scale models, which can be solved concurrently. This relies on a set of relationship between the tracking variables and the output variables, which are physically stored in the memory of the computer and can be reused and retrieved by a plurality of reactor scale models.

In one method, this embodiment is applied to the concurrent simulation of the coating of nanostructured materials under a plurality of deposition conditions, allowing the optimization of the deposition conditions.

In another method, this embodiment is applied to the concurrent simulation of the coating of nanostructured substrate with a material under a plurality of physical systems, allowing the optimization of the physical system in which the deposition of said material is taking place.

Physical systems in which the present invention can be applied include: ALD and CVD reactors, spatial ALD and roll-to-roll systems, batch particle coating reactors such as fluidized bed reactors, and any other physical systems that have been used to carry out the deposition of materials by any of the techniques included in the scope of the present invention.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

In the prior art for reactor-scale ALD applications, for example a 30 cm wafer, the entire structure's scale is vastly larger than the individual elements. Reactor scale is typically on the order of meters while feature scale is on the order of a micron or less (for example trenches, vias, porous nanostructures). Thus predicting ALD behavior of at the reactor scale is difficult. This is especially true where the surface at issue is a high surface area, such as having a number of nanoscale features or structures. The "feature scale" determinations are applied to each discrete unit on the wafer surface while the reactor scale considers the entire 30 cm wafer. It was necessary for each surface element to 1) retrieve the feature state, 2) solve the feature scale model, and 3) update wall boundary conditions. With each surface element computed, the reactor scale equations can be determined. The feature scale model is particularly computation intensive.

In one embodiment, the general feature-scale model is solved, providing a correspondence between the tracking and the output variables. For each time step, every surface element is determined. For each surface element, the tracking variable, in this case the total precursor exposure, is updated, pre-determined values are read, and the wall boundaries are updated based on the output variables retrieved. The reactor-scale equations can them be solved.

The key component of this embodiment is the possibility of identifying both tracking and output variables, a functional relationship between them, and the application of said functional relation to the construction of a look-up table. Hereafter, an example of such an implementation is described based on the simulation of reactive transport at the feature scale using a Markov chain formalism.

As discussed above, methods for modeling non-ideal deposition techniques are needed. Described herein is a method for modeling that addresses the effect of non-ideal ALD surface kinetics in the coating of nanostructure features by introducing a new theoretical framework to model the transport and surface chemistry inside nanostructured features under ALD conditions. By casting the transport inside nanostructures as a single-particle discrete Markov chain process, the method reproduces the results obtained through conventional ballistic transport models while providing the same flexibility as kinetic Monte Carlo simulations in terms of incorporating non-ideal surface kinetics and extracting information on the branching ratios of the different processes. Through this method, one can also able to establish a direct link between ballistic and continuum deposition models and to extract information on the statistics of individual molecules, such as the average number of collisions or the mean residence time on the feature. These expressions are used to understand the validity limits of the single particle and frozen surface approximation implicit in transport models formulated using a particle flux balance approach.

Further, the described single-particle formalism leads to a way of efficiently decoupling the feature and reactor length scales. When the reaction probability does not depend on the local precursor density or flux, the coverage profiles inside a nanostructure are controlled by the total exposure, and not on the details of how the precursor surface flux changed with time in the past.

Models previously have been developed for ALD in nanostructured features. Three approaches have been described in the literature to simulate the coating of high aspect ratio features by CVD and ALD: 1) ballistic models, 2) continuous models, and 3) kinetic Monte Carlo simulations:

Ballistic models compute fluxes at different points of a nanostructure based on a balance of particles:

$$S_i \phi_i = \sum_j q_{ji}(1 - \beta_j - \beta_j^r) S_j \phi_j + q_{0i} S_0 \phi_0 \qquad 2)$$

The flux of molecules reaching a section i of a nanostructure, (e.g., a trench) per unit time, expressed as the flux per unit surface area $\phi_i$ times the surface $S_i$ of the discrete section i of the feature, is equal to the flux arriving from the rest of points in the feature plus the contribution from outside the feature. Here $q_{ji}$ and $q_{0i}$ represent the probability that a particle coming from j in the trench, and 0 outside the trench, respectively, reaches i, and $\beta_j$ and $\beta_j^r$ represent the reaction and surface recombination probability, respectively. The flux arriving from outside the nanostructure is given by $S_0 \phi_0$, where $S_0$ is the area of the opening of the feature. In CVD, this set of equations provides the growth inside a nanostructure. In ALD, this expression determines the evolution of surface coverage inside the nanostructure so that for a section i of area $S_i$ in the nanostructure:

$$\frac{d\theta_i}{dt} = \phi_i s_0 \beta_i(\theta_i) \qquad 3)$$

Here $\theta_j$ is the coverage, and $s_0$ is the average area of a surface site, which can be determined from the ALD growth per cycle. The solution of the local fluxes depends on an independent term that is proportional to the incident particle flux $S_0 \phi_0$, where $\phi_0$ can be expressed as:

$$\phi_0 = \frac{1}{4} v_{th} n \qquad 4)$$

where $v_{th}$ is the mean thermal velocity, and n is the precursor density at the entrance of the feature.

In continuous models, transport inside a nanostructured feature is simulated using a diffusion equation. However, the origin of the diffusion term is not a Fickian diffusion law, but instead appears as a consequence of considering the multiple collisions of a gaseous species with the walls as a random walk process. Based on conductance results, the self-diffusion coefficient can be determined for high aspect ratio pores:

$$D = \frac{1}{3} v_{th} ds \qquad 5)$$

where d is the characteristic size of the feature (diameter for a via, width for a rectangular trench), and s is a non-dimensional constant of the order of one. One of the advantages of modeling particle transport using a diffusion model is that the same nominal equation can be used from the Knudsen to the viscous regime through the use of an effective diffusion coefficient given by:

$$\frac{1}{D} = \frac{1}{D_{Kn}} + \frac{1}{D_{Fick}} \qquad 6)$$

These continuous models have been long used for simulating CVD inside nanostructured features, and a good agreement between their predictions and those of more exact ballistic models has been demonstrated. In the case of ALD, the continuous model leads to the following two equations for a first-order Langmuir model:

$$\frac{\partial n}{\partial t} - D \frac{\partial^2 n}{\partial z^2} = -\beta_0(1 - \theta) \frac{S}{V} \frac{1}{4} v_{th} n \qquad 7)$$

$$\frac{\partial \theta}{\partial t} = -s_0 \beta_0 (1 - \theta) \frac{1}{4} v_{th} n$$

where S/V is the surface-to-volume ratio inside the feature, D is the diffusion coefficient that can be either ballistic, molecular, or in the transition regime, and $\theta$ is the surface coverage as a function of depth and time.

In an earlier work, it was realized that the diffusion process could be treated as a stationary process, so long as:

$$\gamma = \frac{s_0 n V}{S} = \frac{N_V}{N_S} \ll 1 \qquad 8)$$

That is, the frozen surface approximation corresponds to a condition in which a parameter known in the art as the excess number ($\gamma$, number of molecules in the feature per surface reactive site) is much smaller than one. Only then is it possible to establish a steady-state transport, and it is possible to re-obtain the conditions used in Eq. 2 for the ballistic transport models. The excess number is related to the Knudsen number. If the Knudsen number is defined as:

$$Kn = \frac{\lambda}{d} = \frac{1}{dn\sigma} \qquad 9)$$

where $\lambda$ is the particle mean free path, and a is the collision cross section with the background gas, then $\gamma$ and Kn are related through the expression:

$$Kn\gamma = \frac{\lambda}{d} = \frac{s_0}{4\sigma} \qquad 10)$$

Alternatively, a third prior art model, the kinetic Monte Carlo simulations, essentially envisions the coating of a nanostructured feature from a single-molecule perspective. This molecule will undergo a number of collisions until either leaving the feature or irreversibly adsorbing inside the feature. This is the approach followed by Monte Carlo simulations. Implicit in this approach is again that the change in surface coverage takes place at a slower rate than the characteristic time for particle adsorption in order to ensure the validity of the single-particle approximation. Therefore, the frozen surface approximation that appeared naturally in the context of continuous models also is utilized in the Monte Carlo simulations. Monte Carlo simulations also allow the determination of the average time that a molecule takes to react (or eventually leave) the nanostructure and thereby the evaluation of the validity of the frozen surface assumption. However, the downside of kinetic Monte Carlo simulations is that they require the accumulation of a sufficiently large number of trajectories in order to achieve good statistics, making integration with reactor-scale models computationally intensive.

Although these prior models exist, they are insufficient. As described in further detail below, the present invention describes a method that provides the same desired results as the conventional flux approach of the ballistic model while preserving the time information provided by kinetic Monte Carlo simulation. By moving from an ensemble to a single-particle approach, the optimum strategy to couple feature and reactor length scales also becomes transparent, leading to a much faster integration of the two length scales. The benefits derived from this approximation include: faster calculation, the possibility to simulate a plurality of different systems using the same algorithm, an increase in accuracy compared to kinetic Monte Carlo methods and the possibility of decoupling the feature scale from the reactor scale components in the simulation.

One embodiment of the present invention relates to a Markov chain model for ALD in nanostructured features. In this work, the transport of reacting molecules is cast inside a feature as a Markov chain process. That is, the trajectory of a molecule inside the nanostructure is pictured as a series of transitions between different states, which represent the geometrical position of the particle on the surface of the feature and how the particle is bound to the surface.

A Markov chain is defined as a set of states $\alpha_i \rightarrow \alpha_j$ and the corresponding probabilistic transition rules between these states $p_{\alpha_i\alpha_j}$. Using the nomenclature of Markov chain processes, these states can be either transient (if the states can transition to other states) or absorbing (if the states represent 'end game' situations). In the context of ballistic transport, the particle collision with the walls is pictured as a set of transitions between different points in the feature $i \rightarrow j$. In addition to this, there are two other options: either the particle escapes from the feature, $i \rightarrow 0$, or it irreversibly reacts with the surface.

The number of absorbing states used to model surface reactivity depends solely on the amount of information that one is interested to gain from the model. At minimum, one needs at least two absorbing states, one for each of the two outcomes of the process: either the particle leaves or it reacts within the feature. But in this case, the model does not provide any information on where in the feature the particle reacts. To gain this knowledge, one needs to consider at least one absorbing state for each spatial point i of the feature and define the transition probability $i \rightarrow F_i$. However, this level of detail does not yet provide information on the mechanism leading to the irreversible interaction of the precursor molecule with the surface i of the feature when there is more than one reaction pathway. The next step is therefore to consider one independent absorbing state (or channel) per reaction pathway at each point of the feature and define the corresponding transition probabilities $i \rightarrow F_i^j$. A scheme for the transitions between the different states in the model is shown in FIG. 1.

The feature being considered can be discretized into N sections, thus providing N transient states (the weakly adsorbed surface states), and in the most general case $n_s$ N+1 for $n_s$ surface channels. The absorbing states define all of the possible outcomes for a particle in the feature. Note that the solution of the Markov chain is independent of the meaning that assign to each channel. That is, only the transition probability is needed for each surface kinetics channel. For instance, if surface recombination is allowed for in addition to irreversible absorption on the surface, then two separate channels $i \rightarrow F_i$, $i \rightarrow R_i$ are defined. Therefore, a plurality of reaction mechanisms can be considered by identifying each of them with a different reaction channel. As an example, one can consider a spurious CVD reaction pathway by defining an additional channel with the associated transition $i \rightarrow C_i$. By assigning a separate channel in the Markov chain model, one can extract information on the impact of each separate reaction pathway.

In all the cases defined above, the set of all possible transition probabilities is defined by a transition probability matrix, $P_{\delta\gamma}$. For the case of two reaction channels, adsorption and recombination, characterized by probabilities $\beta_i$ and $\beta_i^r$, these transition probabilities can be calculated using the following expressions:

$$P_{ij} = (1 - \beta_i - \beta_i^r) q_{ij}$$

$$P_{i0} = (1 - \beta_i - \beta_i^r) q_{i0}$$

$$P_{iF_i} = \beta_i$$

$$P_{iR_i} = \beta_i^r \qquad 11)$$

where the $q_{ij}$ and $q_{i0}$ are the reemission probabilities of the ballistic model introduced in Eq. 2, and $\beta_i + \beta_i^\tau \le 1$. The Markovian character of this process comes from the fact that the probability that a particle exists in the state $\gamma$ after m collisions, $p_\gamma(m)$, depends only on where it underwent the previous collision:

$$p_\gamma(m) = \sum_\delta P_{\delta\gamma} p_\delta(m-1) \qquad 12)$$

The starting condition is determined by the geometry of the feature. If a particle originating from outside the feature reaches section i of the nanostructure with a probability $\pi_i$, then define $p_i(1) = \pi_i$. The $\pi_i$ can be estimated from the velocity distribution function of the particles at the entrance of the nanostructure and the solid angles of each section of the feature.

By formulating the problem as a Markov chain, not only are the probabilities a function of the number of collisions using Eq. 12, but the theory of Markov chains can be used to extract all the relevant information for an ALD process. General expressions for the absorption probabilities, escape probability and effective reaction probability of the feature and the average number of collisions are given below. Equations 44-47 provide the information to understand the coating of nanostructured features, and they are applicable to both ALD and CVD. In one embodiment, single-particle kinetic Monte Carlo simulations provide this information by sampling a large enough number of trajectories. Here, the information can be extracted by simply calculating M, that is by carrying out a matrix inversion to determine the outcome of the Markov process and all its associated characteristics. The output of this method provides the effective sticking probability.

The probabilistic out-come of an absorbing Markov chain can be determined as follows. The probability matrix P, containing all the transition probabilities between the states in the model, can always be expressed in the so-called standard form, in which the rows are ordered starting from the absorbing states, followed by the transition states. When the states are ordered in such a way, P is represented as a block matrix:

$$P = \begin{bmatrix} I & 0 \\ R & Q \end{bmatrix} \qquad 41)$$

where I is the identity matrix, Q is the matrix containing the transition probabilities between transient states, and R is the matrix containing the transition probabilities from transient to absorbing states. From this matrix, all the relevant information for the transport inside a nanostructured feature can be extracted.

Adsorption and recombination probabilities: The probability that a precursor molecule irreversibly adsorbs in section j is given by:

$$P(j) = \sum_i \pi_i (MR)iF_j = \beta_j \sum_i q0iMij \qquad 42)$$

where M is the matrix defined as:

$$M = (I-Q)^{-1} \qquad 43)$$

Likewise, the probability that a species undergoes surface recombination in j is given by:

$$P_{rec}(j) = \beta_j^r \sum_i q0iMij \qquad 44)$$

For more than one surface reaction pathway, then $P_{cj}$ (i) for every possible reaction pathway in the surface.

Effective Reaction Probability

The probability that a precursor molecule escapes the feature without undergoing a reaction is given by:

$$P(0) = \sum_i \pi_i (MR)_{i0} \qquad 45)$$

which means that the effective reaction probability observed by an incoming particle in the trench will be given by:

$$\bar{\beta} = 1 - \sum_i \pi_i (MR)_{i0} \qquad 46)$$

Average Number of Collisions

The average number of collisions of a particle bouncing inside the nanostructure is given by:

$$N_c = \sum_{ij} q0iMij \qquad 47)$$

In one embodiment, the ballistic Markov chain model is applied to the evolution of surface coverage in ALD. The Markov chain model described above allows decoupling the transport and reaction inside the nanostructured feature from the details of the surface kinetics controlling the irreversible reaction of the precursor with the surface. As mentioned in the previous section, the outcome of the Markov chain model is the probability P(i) that a particle in section i adsorbs on the surface. For an incident flux given by $S_0\phi_0$, a link is established between P(i), the local reaction probability for section i, $\beta_i$, and the local flux of precursor molecules reaching section i, $S_i\phi_i$:

$$S_0\phi_0 P(i) = \beta_i S_i \phi_i \qquad 13)$$

Figure 2:
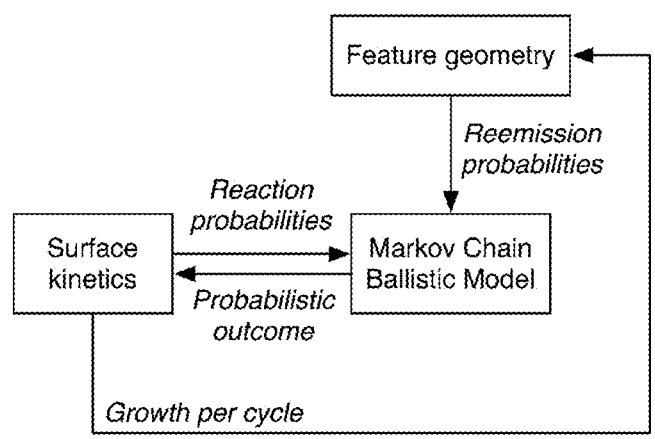
FIG. 2 illustrates a scheme of the model used in this work, showing the coupling and interdependence between the Markov chain transport, the surface kinetics, and the feature geometry components.

In the case of a steady-state process like CVD, Eq. 13 would directly translate into the growth rate at each point of the feature. However, in the case of ALD, the local reaction probability is going to depend on the local surface coverage. Therefore, the Markov chain model needs to be coupled with a surface chemistry model. The way in which the surface chemistry and Markov Chain ballistic transport model are coupled is shown in FIG. 2. FIG. 2 also considers the update of the feature shape due to film growth, for instance using the methods outlined in earlier works in the literature.

By applying Eq. 13 directly to Eq. 3:

$$\frac{d\theta_i}{dt} = \phi_i s_0 \beta_i(\theta_i) = s_0 \frac{S_0}{S_i} \phi_0 P(i) \qquad 14)$$

And this is true for a general $\beta_i(\theta_i)$, which may include not just first-order but higher-order dependence of the reaction probability with the surface coverage. This is a particular example of the more general case:

$$\frac{d\beta_i}{dt} = f(\phi_i; v_i) \quad 15)$$

where $v_i$ represent the set of internal variables controlling the value of the effective reaction probability. These will depend on the particular particle-reaction model considered and can be calculated by methods established in the prior art, such as Density Functional Theory calculations, kinetic Monte Carlo simulations and molecular dynamics, or can be measured experimentally. The combined solution of the Markov Chain model, and Eq. 15 would provide the evolution of reaction probability with time in the same way as the flux based ballistic model, with Eq. 15 playing the role of the surface chemistry module depicted in FIG. 2.

This result can be generalized to the situation when there are $n_s$ independent reaction channels, including both recombination and spurious CVD. Likewise, when the self-limited ALD process is best represented by more than one surface reaction pathway, it is also possible to break this down into separate components that facilitate calculation of the contribution of each pathway to the ALD process. In this case, the total probability of a particle reacting at a point i is the sum of all of the independent reaction channels:

$$P(i) = \sum_{n_a} P_j(i) \quad 16)$$

If each channel occupies a fraction of sites $f_j$, then each channel can be modeled in terms of its own fractional coverage $\theta_{ij}$ so that there is a vector of surface coverages $\theta_i$; and reaction probabilities $\beta_i$, linked through a general equation $\beta_i(\theta_i)$, and a time evolution of each fractional coverage given by:

$$\frac{d\theta_{ij}}{dt} = \phi_i s_0 f_j \beta_{ij}(\theta_i) = s_0 \frac{S_0}{S_i} \phi_0 P_j(i) \quad 17)$$

First order dependence with particle flux is exhibited. Equations 14 and 17 share in common the fact that the change in surface coverage of each self-limited reaction pathway is first order in the precursor flux to the surface, that is, the reaction probability is independent on the precursor density and only depends on surface variables. Under these conditions, it is possible to further simplify the problem and show that the coating of the feature depends only on the total precursor exposure and not on how that exposure is distributed in the past.

First, the total exposure, $\psi$, is defined as the number of precursor molecules that have entered the feature up to a certain time:

$$\Psi = S_0 \int_0^t \phi(t')dt' = S_0 \frac{1}{4} v_{th} \int_0^t n(t')dt' \quad 18)$$

Since the surface chemistry is controlled by only one species, a one-to-one relation can be established between time and the total precursor exposure so that:

$$\frac{d\theta_i}{dt} = \frac{d\theta_i}{d\Psi}\frac{d\Psi}{dt} = \frac{d\theta_i}{d\Psi}S_0\phi(t) \quad 19)$$

and therefore:

$$\theta_i(t) = \int_0^t \frac{d\theta_i}{dt'}dt' = \int_0^t \frac{d\theta_i}{d\Psi}\frac{d\Psi}{dt'}dt' = \int_0^\Psi \frac{d\theta_i}{d\Psi}d\Psi = \theta_i[\Psi(t)] \quad 20)$$

This means that the surface coverage at a given time is determined by the total number of precursor molecules that have entered the feature, and not on the detailed temporal evolution of the incident flux (i.e., the "pulse shape" of the precursor dose. The total exposure, $\psi$, completely characterizes the state of the feature. Consequently, a plurality of pulse shapes can be simulated using the functional relationship between the total exposure and the state of the feature. This model can be used to generate a general look-up table based on the total exposure, that can be applied to a plurality of reaction configurations. The same lookup table can be used to simulate the effect of the nanostructured material at every point of the reactor.

Having accounted for surface coverage, it is now possible to formulate the model in terms of the total exposure. From Eq. 14:

$$\frac{d\theta_i}{dt} = S_0\phi_0\frac{s_0}{S_i}P(i) = S_0\phi_0\frac{s_0}{S}\frac{S}{S_i}P(i) = \frac{S_0\phi_0}{N_s}\left[\frac{S}{S_i}P(i)\right] \quad 21)$$

Here, $N_S$ is the total number of surface sites available inside the feature, and the bracketed term depends only on the relative dimensions, since the surface area at each section i is normalized by the total surface area.

From here:

$$\frac{d\theta_i}{d\Psi} = \frac{1}{N_s}\left[\frac{S}{S_i}P(i)\right] \quad 22)$$

Likewise from Eq. 17:

$$\frac{d\theta_{ij}}{d\Psi} = \frac{1}{S_0\phi_0}\frac{d\theta_{ij}}{dt} = \frac{1}{N_{S_j}}\left[\frac{S}{S_i}P(i)\right] \quad 23)$$

Here $N_{Sj}=S/S_{0j}$ is the number of j surface sites in the feature. Equations 22 and 23 contain all the information required to model the ALD process inside a nanostructure during a single dose, with the time dependence contained in $\psi(t)$. This will depend on how efficiently the precursor is transported inside the reactor to that particular point of the surface.

The link between total exposure and the state of the trench can also be applied to CVD in the transport-limited regime, that is, as long as site-blocking effects are not important. However, it is not necessary to keep track of the surface coverage, and instead the evolution of the feature size with total exposure would determine the change in the effective sticking probability (output variable).

The ability to describe the state of a nanostructured materials and the relevant output variable as a function of a single tracking variable such as the total exposure, allows the decoupling of the feature and reactor scale models. Instead of solving them concurrently, the output of the feature scale model can be stored in a database and applied to solve a plurality of systems. Given a reactor-scale model, the effective sticking probability as a function of total exposure can be applied both at the boundary conditions, or to model precursor consumption by particles suspended in the gas phase using, for instance, lagrangian particle models or other approaches that are part of the art.

Through this method, the relevant surface kinetic data determined under one condition can be used to simulate the feature-scale data and then applied to concurrently solve the deposition under a wide range of experimental conditions, allowing a fast optimization of the process. Likewise, by applying this method in conjunction with optimization algorithms described in the prior art, the reactor design can be optimized to maximize the quality or the value of a deposition process.

Finally, this method can be applied to the design of engineered nanomaterials, including, but not limited to, core-shell nanostructured electrodes, core-shell particles, and the conformal coating with multilayers of high aspect ratio features and recessed substrates using the processing methods targeted by this invention.

Examples

The above described Markov chain model can be applied in one embodiment to study ALD inside of nanostructured features. Although example implementations herein may describe closed circular vias (pores) of arbitrary aspect ratio, as a function of the surface reaction probability, the method may be applied to other nanostructured features as well. One advantage of using these structures is that they have been the subject of previous studies, and this will allow benchmarking of the validity of the Markov chain model. Thus, the changes are evaluated not as a function of time, but as a function of the total exposure, given the one-to-one dependence between these two variables that can be established in the self-limited irreversible Langmuir case. All the results here have been carried out using uniformly discretized sections and a single section for the bottom of the feature, leading a value of N=201. The entry probabilities $\pi_i$ and transition probabilities between discrete sections have been determined using the standard expressions of conventional ballistic models under a cosine reemission law.

Benchmarking the Markov Model

Considering first the simplest case of a single surface channel in which the ALD surface kinetics is modeled as an irreversible first-order Langmuir kinetics. From Eq. 22, it is easy to see that if the normalized exposure $\xi = \psi/N_S$ is defined as the number of incident molecules per surface site in the feature, then:

$$\frac{d\theta_i}{d\left(\frac{\psi}{N_S}\right)} = \frac{d\theta_i}{d\xi} = -\left[\frac{S}{S_i}P(i)\right] \qquad 24)$$

giving $\theta_i = \theta_i(\psi/N_S)$. This means that the exposure required to achieve a certain coverage scales linearly with the total number of surface sites of a feature. This also allows focus on the coverage as a function of the normalized exposure, $\theta_i = \theta_i(\xi)$, since from this expression the evolution of coverage for any feature size can be trivially obtained.

Figure 3:
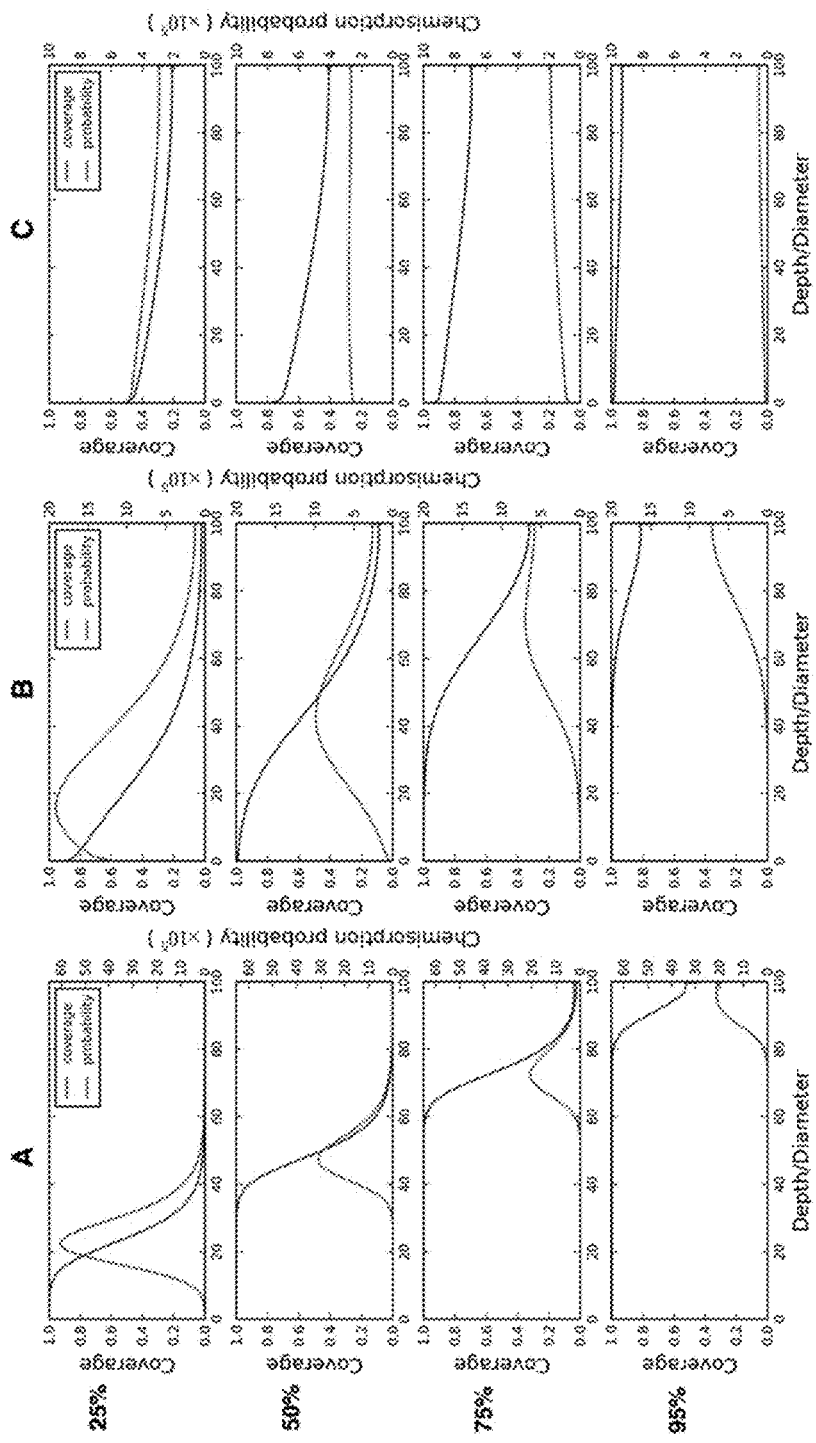
FIG. 3 illustrates normalized coverage profiles and reaction probabilities at 25, 50, 75 and 95% total coverages for the following bare reaction probabilities: $\beta_0=0.01$ (a), $\beta_0=0.001$ (b) and $\beta_0=0.0001$ (c).

FIG. 3 shows coverage profiles obtained for 25, 50, 75, and 95% total coverage for an AR=100 feature using bare reaction probabilities of 0.01, 0.001, and 0.0001. As the bare reaction probability decreases, the coverage profiles change from a step-like shape to become almost constant with position in the feature, in agreement with previous reports. FIG. 3 also shows the reaction probability as a function of position for each set of conditions, showing that as the bare reaction probability increases, the area over which reaction occurs narrows and approaches the ideal situation of an abrupt saturation front as assumed by prior research (see Gordon et al.). One well-known difference between the ballistic and diffusion models is the contribution of the precursor flux directed at the bottom of the trench. Due to the larger solid angle of the bottom section of the pores, the coverage at the bottom of the feature is greater than the coverage on the nearby sidewalls.

The simulations also allow calculation of the normalized exposures required to coat the features. As mentioned above, an analytic expression for the exposures required to coat nanostructured substrates based on the analytic continuation of the low- and high-reaction probability limits is reflected in (Eq. 1). Using the definition of total exposure $\phi$ and $N_s$, Eq. 1 can be expressed asas:

$$\Psi_{end}/N_s = \frac{3}{2}\frac{(AR)^2}{1+4(AR)}\left(1 - \frac{2\log(1-c_0)}{3\beta(AR)^2}\right) \qquad 25)$$

Figure 4:
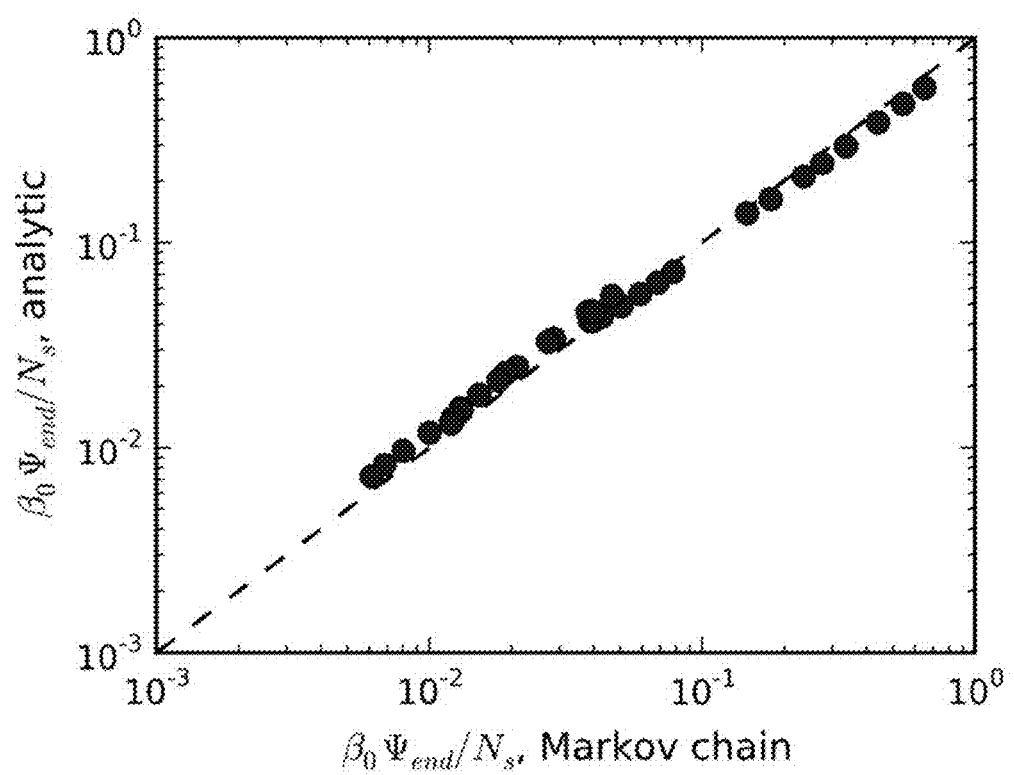
FIG. 4 illustrates a correlation between the time to coat from the analytic formula (Eq. 25), and from the Markov Chain ballistic model. Exposures $\psi$ are presented normalized to the number of surface sites in the features $N_s$ and the reaction probability $\beta_0$.

$\psi_{end}$ is defined as the exposure required to coat 99.9% of the active sites in the feature. In FIG. 4, the normalized exposure times are plotted for bare reaction probabilities in the range $\beta_0 = 10^{-5} - 10^{-2}$ and AR=50-250 calculated using the Markov chain model against Eq. 25 predicted by the analytic model. FIG. 4 shows an excellent correlation between the two models, emphasizing the quantitative agreement between the Markov chain approach and the previous approaches used in the literature. Still, some small differences can be observed for small $\psi_{end}/N_s$ values. These correspond to the diffusion-limited regime, and the departure from the 1:1 correlation is due to the limitations of the continuous approximation breaking down for low aspect ratio features. By modeling transport as a diffusive process, it disregards the direct line-of-sight contribution to the bottom of the trench. The relative contribution of this component becomes more relevant for higher reaction probabilities, which correlates as shown in FIG. 3, column C, with the transport-limited regime. Secondly, Eq. 1 is defined as the time required to achieve a coverage $c_0$ at the bottom of the feature. Despite these small differences, FIGS. 3 and 4 confirm that the approach described in this work is physically correct.

State of the Feature as a Function of Integrated Incident Exposure

A key result from the previous discussion above regarding benchmarking the Markov model was that when the reaction probability does not depend on the precursor pressure, the surface coverage inside a feature depends not on the detailed temporal profile of the exposure, but only the integrated incident exposure, $\psi$ (Eq. 24). In this section, the state of the feature as a function of this parameter is discussed. For ease of comparison, the different magnitudes are plotted against $\psi/\psi_{end}$, where $\psi_{end}$ was defined above (Eq. 25).

Figure 5:
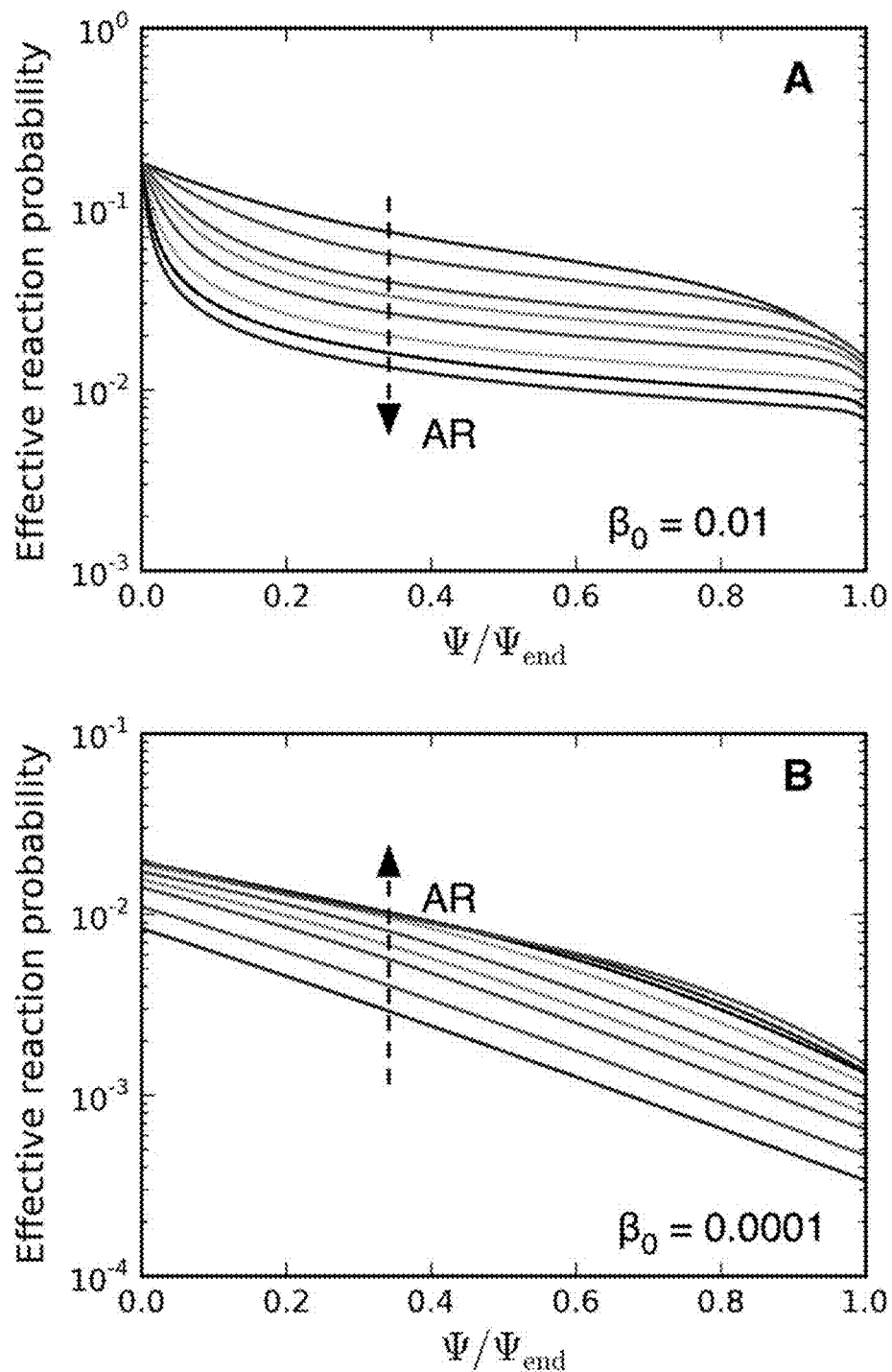
FIG. 5 illustrates an effective reaction probability as a function of total exposure for two different bare reaction probabilities: a $\beta_0=0.01$ and b $\beta_0=0.0001$, and increasing aspect ratios AR. Exposures are normalized to the end exposures required to completely coat the trench.

FIGS. 5a, b show the evolution of the effective reaction probability for different aspect ratios AR=25-300 and bare reaction probabilities of $\beta_0$=0.01 and 0.0001, respectively. A comparison of the functional dependence of the reaction probability in these two figures reveals the presence of two limiting cases. When the bare reaction probability and aspect ratio are low enough, the reaction probability evolves with exposure following the same functional form as the flat surface. According to the first-order irreversible Langmuir kinetic used for these calculations, this corresponds to a straight line in the semilogarithmic plots of FIG. 5. In this limit, the initial effective reaction probability depends on the aspect ratio, as it represents simply an increase in the number of reactive sites per unit wall surface area. This corresponds to the reaction-limited case. The analytic expression for this case can be easily derived: using Eq. 13, providing that $S_0\phi_0 P(i)=\beta_i S_i\phi_i=\beta S_i\phi_0$ so that:

$$\beta_{\text{eff}} = \sum_i P(i) = \beta\frac{S}{S_0} = \beta_0\frac{S}{S_0}(1-\theta) \qquad 26)$$
$$= (1+4(AR))\beta_0(1-\theta)$$

where $S=\pi dL+S_0$, $S_0=\pi d^2/4$, and $(AR)=L/d$. This means that $(\beta_{\text{eff}}^0=(1+4(AR))\beta_0$.

Conversely, as the bare reaction probability and aspect ratio become large enough, the initial effective reaction probability becomes independent of the aspect ratio. The features appear as infinitely long reacting pores. As the pores start to get coated, they do so with the step profiles shown in FIG. 3, column A, so the effective probability evolves with coverage following Clausing's model of transport through a finite cylindrical tube. This behavior was formerly identified in the prior art and used in deriving a limiting expression of Eq. 1 for high-reaction probabilities.

Figure 6:
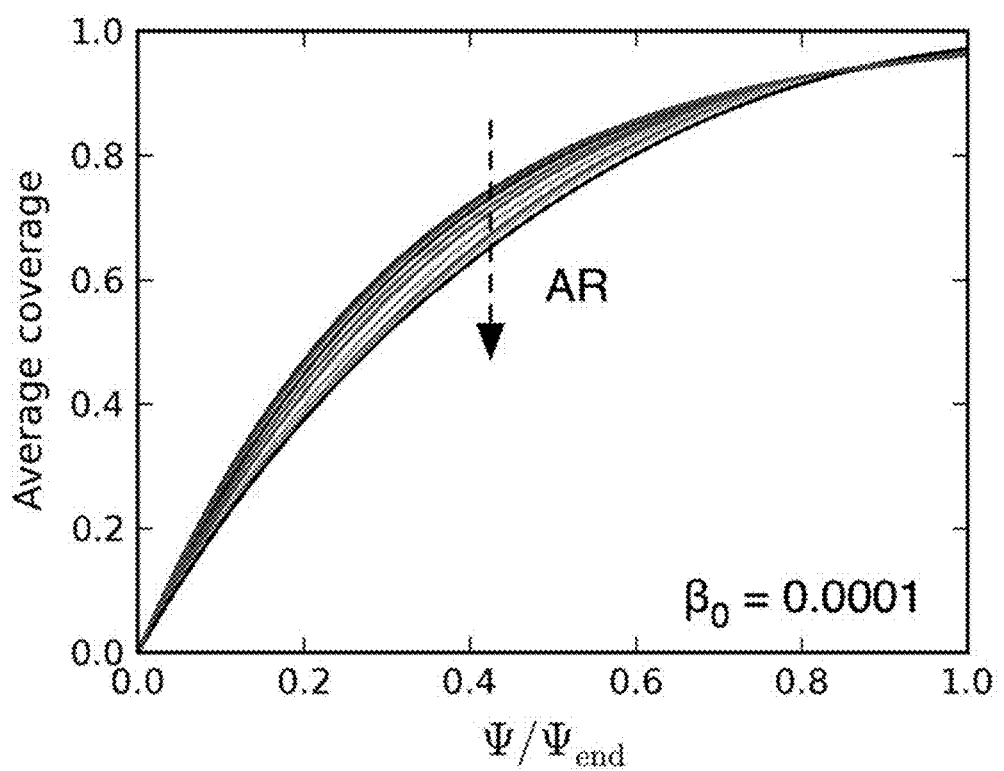
FIG. 6 illustrates an average coverage with total exposure for a bare reaction probability $\beta_0=0.0001$ and increasing aspect ratios, AR. Exposures are normalized to the end exposures required to completely coat the trench.

The change in the average surface coverage with the total exposure is shown in FIG. 6 for a bare reaction probability of $\beta_0$=0.0001, and increasing aspect ratios. A transition is observed with increasing aspect ratio, ranging from the functional form characteristic of first-order irreversible Langmuir kinetics, to a square root dependence with exposure, signifying a diffusion-dominated process. In the low reaction probability limit, where the process is limited by surface kinetics and not precursor transport, multiscale models coupling feature and reactor scales are trivial. The impact of high-surface area substrates can be modeled at the reactor scale as regions with a larger effective number of surface sites per unit surface area so as to reproduce the uptake curves depicted in FIG. 6.

An example of how the Markov chain approach descried herein can easily accommodate more complex surface kinetics is shown by considering the impact of having two kinds of reactive sites on the surface, each characterized by its own bare reaction probability. This approach could be used, for instance, to model surface reactivity based of ligand exchange with surface hydroxyls and dissociative chemisorption as two separate reaction channels whose overall branching ratios are determined by the density of surface hydroxyls. In this case, the total coverage will be given by:

$$\theta=f_1\theta_1+f_2\theta_2 \qquad 27)$$

where $f_1$ and $f_2$ are the relative proportions for the two types of sites and $\theta_1$ and $\theta_2$ are the corresponding fractional coverages. Assuming first-order irreversible Langmuir kinetics for each component then:

$$\frac{d\theta_1}{d\Psi} = \beta_1(1-\theta_1) \qquad 28)$$
$$\frac{d\theta_1}{d\Psi} = \beta_1(1-\theta_1)$$

In the case of a flat surface the evolution of surface coverage with exposure will be given by:

$$\theta(\Psi) = (1-f)(1-e^{\beta_0\Psi}) + f(1-e^{r\beta_0\Psi}) \qquad 29)$$

where $\frac{\beta_2}{\beta_1} = r$, $\beta_1 = \beta_0$ and $1-f_2 = f_1 = f$.

Figure 7:
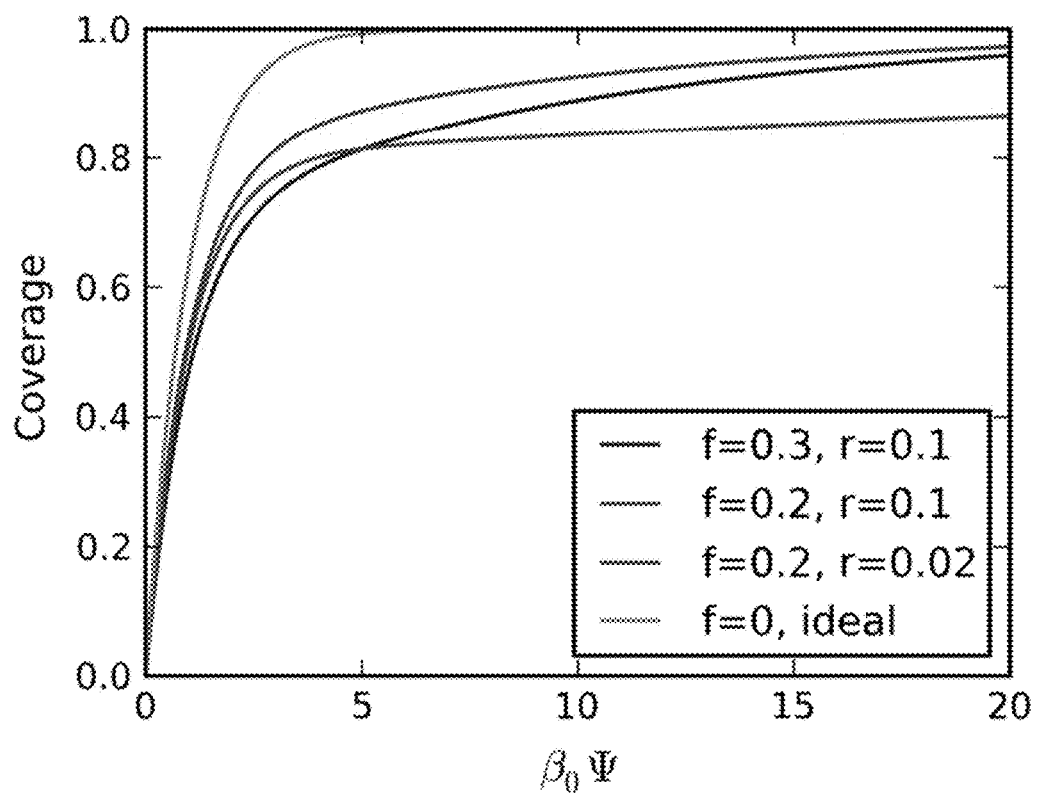
FIG. 7 demonstrates the impact of a second, lower reaction probability channel in the saturation curve of a self-limited first-order irreversible Langmuir model. As specified in the legend, each curve represents a different fraction of surface sites, f, and relative reaction probability for the secondary channel, r.

A plot of $\theta(\psi)$ is shown for selected values of r and f in FIG. 7. Depending on the values of f and r, the resulting saturation curves could be misinterpreted as signifying either nonself-limiting CVD (f=0.3, r=0.1), or a low growth per cycle (f=0.2, r=0.02).

Figure 8:
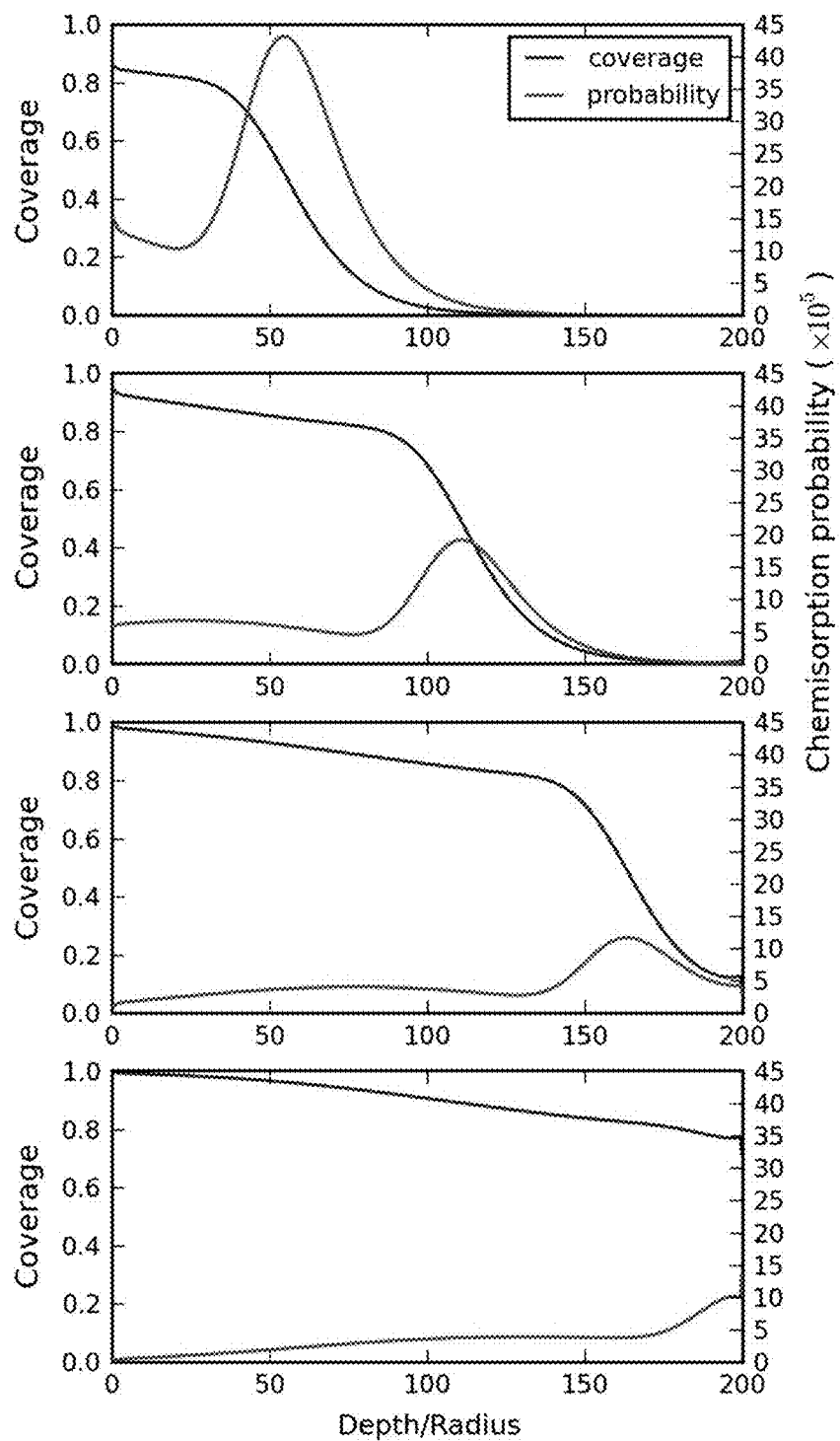
FIG. 8 illustrates a coverage profile and chemisorption probability at 25, 50, 75, and 90% total surface coverage for a two-site model with reaction probabilities: 0.01 (80%) and 0.001 (20%).
Figure 9:
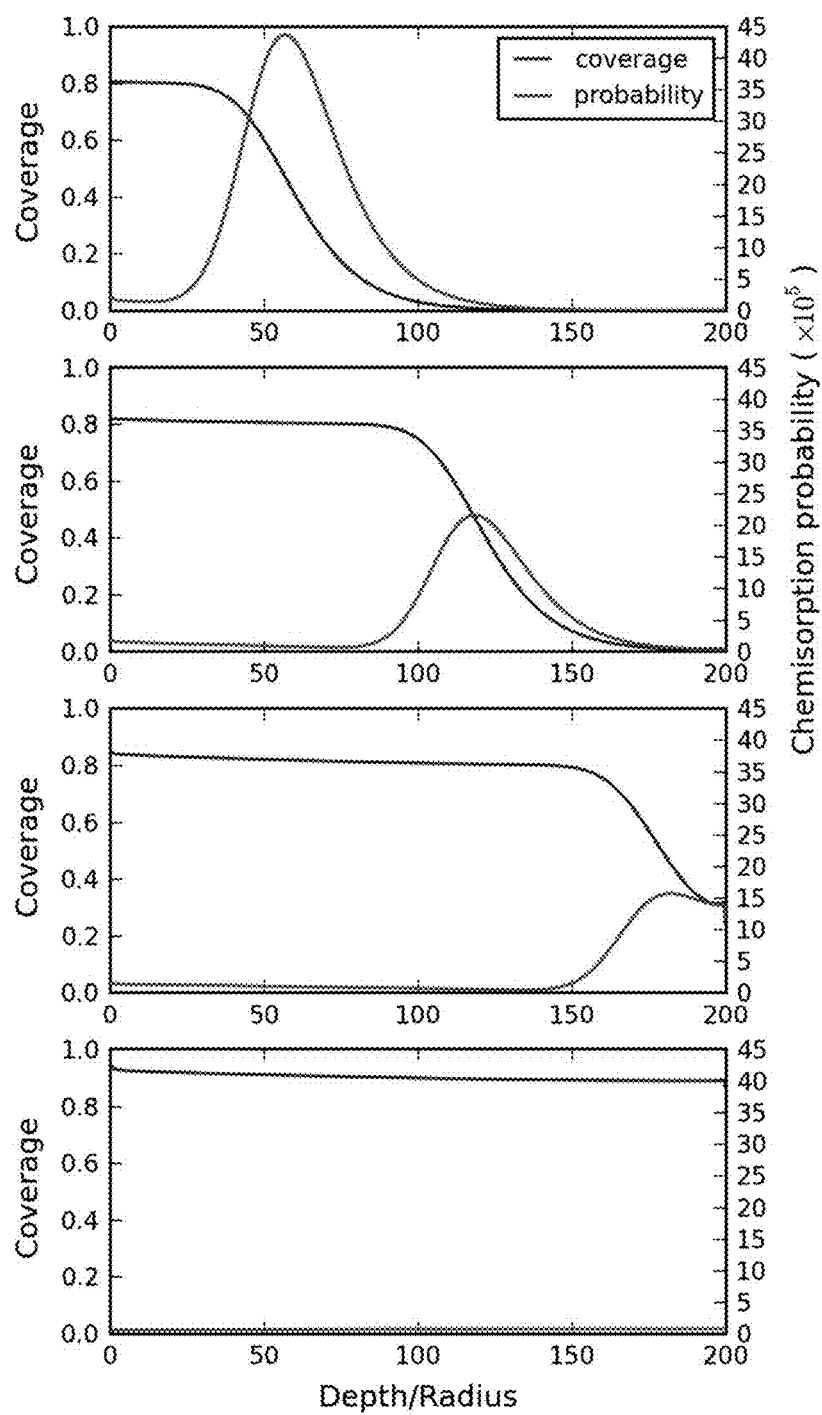
FIG. 9 illustrates a coverage profile and chemisorption probability at 25, 50, 75, and 90% total surface coverage for a two-site model with reaction probabilities: 0.01 (80%) and 0.0001 (20%).

FIG. 8 shows the profiles and the reaction probability at 25, 50, 75, and 95% coverage for $\beta_1$=0.01, $f_1$=0.8, $\beta_2$=0.001, and $f_2$=0.2. A comparison between FIGS. 8 and 3 shows how the filling of a feature follows an initial behavior that is similar to the single site absorption, but instead of reaching saturation, there is a fraction of sites that react more slowly. This affects the probability for absorption. While in FIG. 3 the probability is narrowly centered on the saturation front, in FIG. 8 there is a substantial reaction probability close to the entrance of the pore even at later times. One of the implications of having such a low reaction probability tail is that cross-sectional characterization of coated features may give the false impression of complete saturation, whereas in reality the homogeneity of the profile is a consequence of the small reaction probability of the second surface reaction path-way, as it is well known from the CVD case. This is shown in FIG. 9, which presents profiles and reaction probability for the same conditions as in FIG. 8, except that now the second reaction pathway has a reaction probability two orders of magnitude smaller, $\beta_2$=0.0001. The effects of non-ideal ALD surface kinetics driven by more than one independent surface reaction pathway are expected to be more prevalent in large-area substrates in which different points of the feature are expected to see widely different total exposures. Features may appear homogeneously coated, yet have a gradient in film thickness as a consequence of the low reaction probability tail of the saturation curve.

Finally, one important consequence of the dependence with total exposure is that it greatly simplifies the implementation of multiscale ALD models that include both feature- and reactor-scale processes, essentially making them as fast as the corresponding models on flat surfaces. This approximation has been used to carry out extremely fast simulation of the coating of large substrates with high aspect ratio features in cross-flow reactors. However, it is well known from CVD that when the growth is mediated by intermediate, weakly bonded species, the reaction probability decreases with precursor pressure, due to the self-limiting nature of surface reaction processes with respect to precursor adsorption, resulting in site-blocking. The advantages of a linear dependence with flux are lost in these cases, and the dependence of the state of the feature with the total coverage breaks down.

Figure 11:
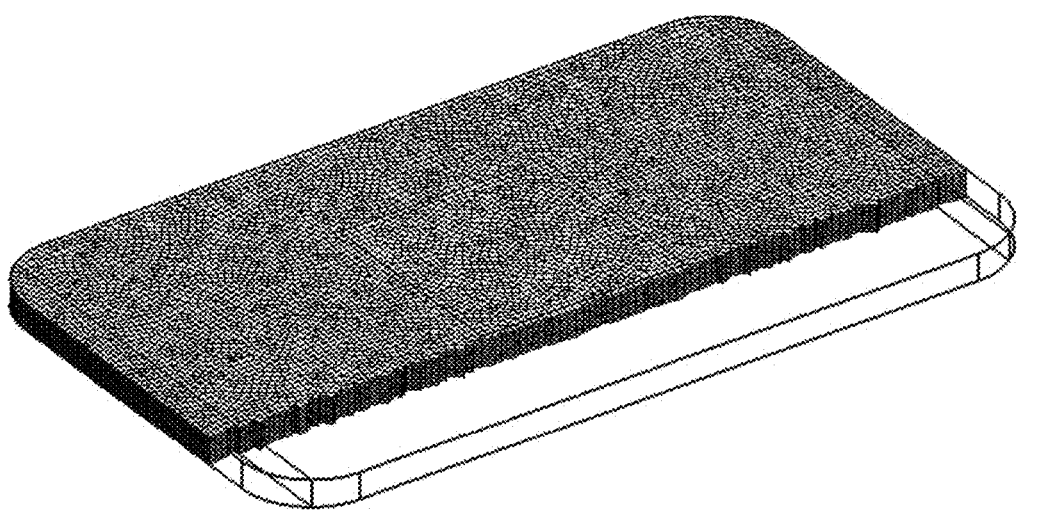
FIG. 11 illustrates a simulation domain for the coating of a 6×6 in nanostructured material in a cross-flow ALD reactor
Figure 12:
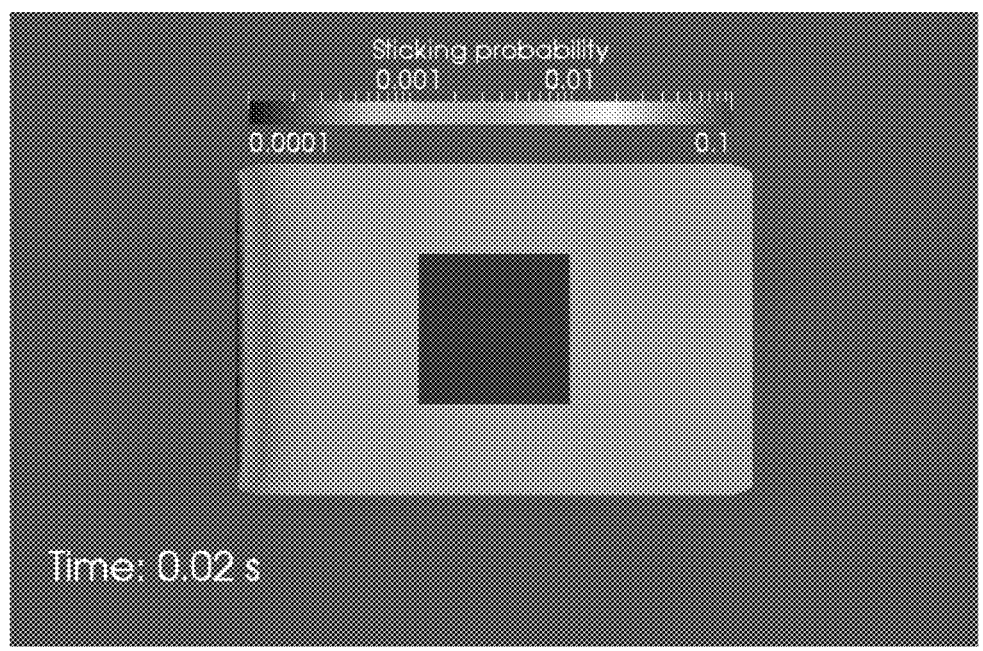
FIG. 12 illustrates a simulation of the coating of a 6×6 inch high surface area material in a cross-flow reactor using the method described in the invention: initial sticking probability
Figure 13:
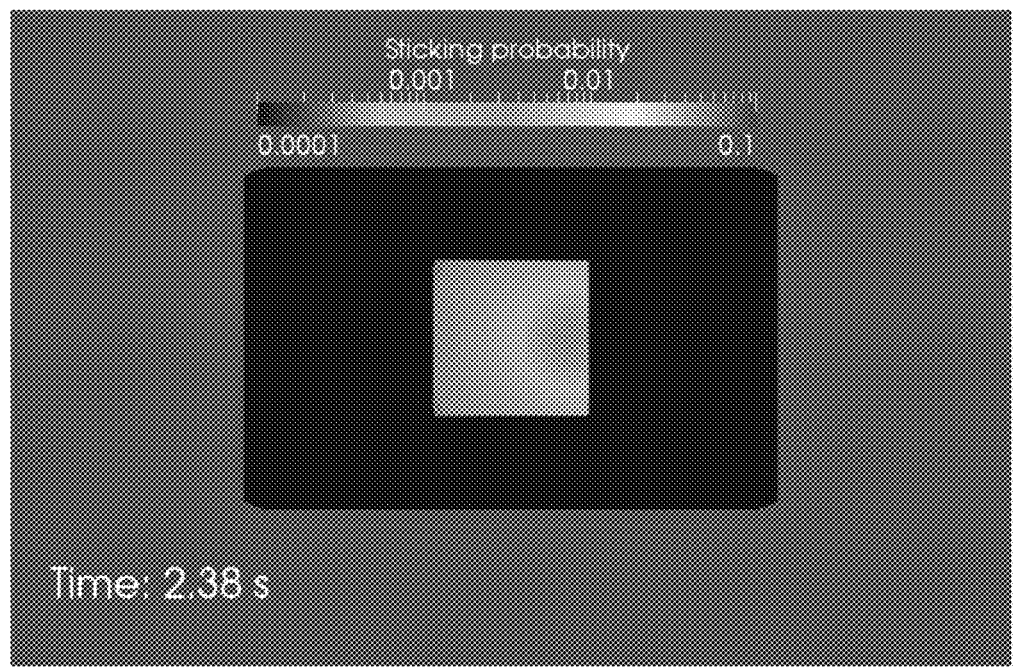
FIG. 13 illustrates a simulation of the coating of a 6×6 inch high surface area material in a cross-flow reactor wherein the final sticking probability is not homogeneous as a consequence of the large surface area material being inhomogeneously coated.
Figure 14:
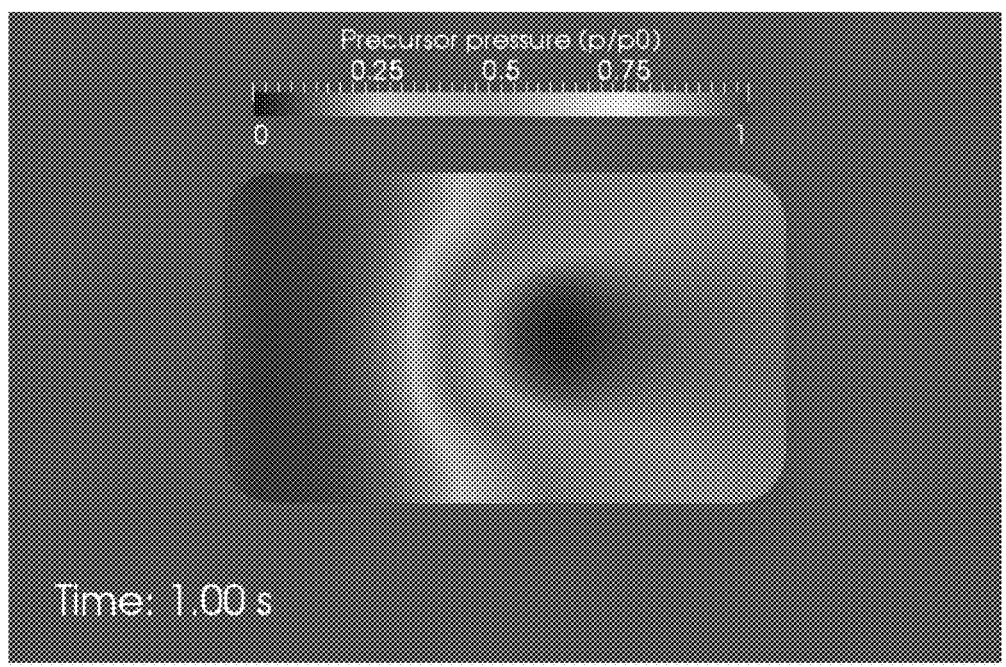
FIG. 14 illustrates the effect of the presence of a high surface area material on the precursor pressure at a reactor scale wherein precursor pressure mid height of the deposition reactor after 1 s, showing how precursor depletion is responsible for the spatial inhomogeneities.
Figure 15:
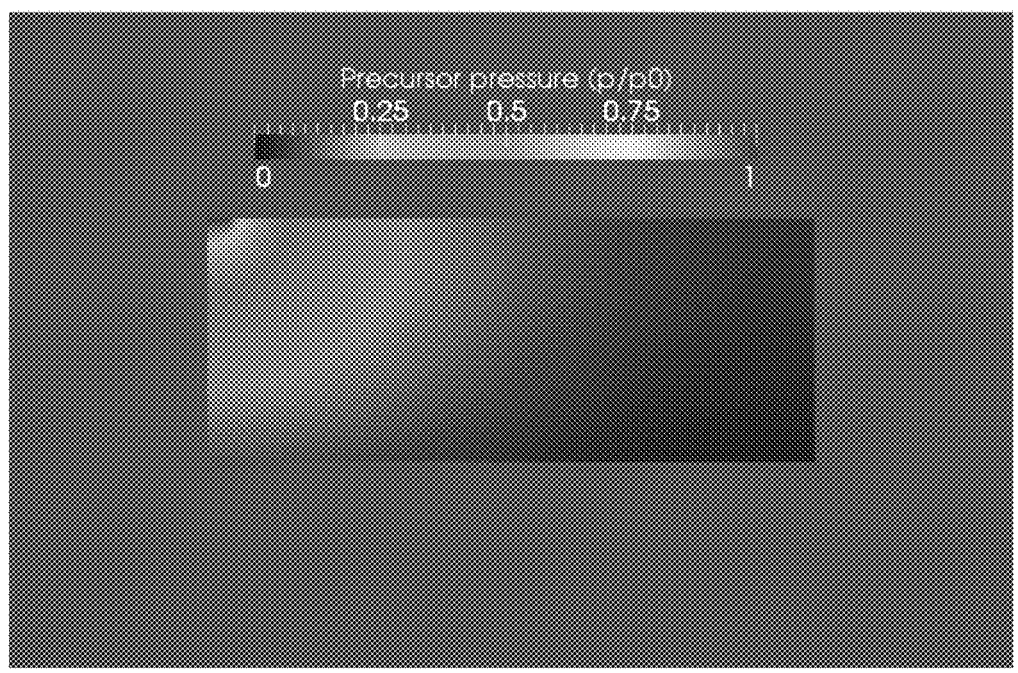
FIG. 15 illustrates precursor depletion due to the coating of a nanostructure material in a roll-to-roll set up.
Figure 16:
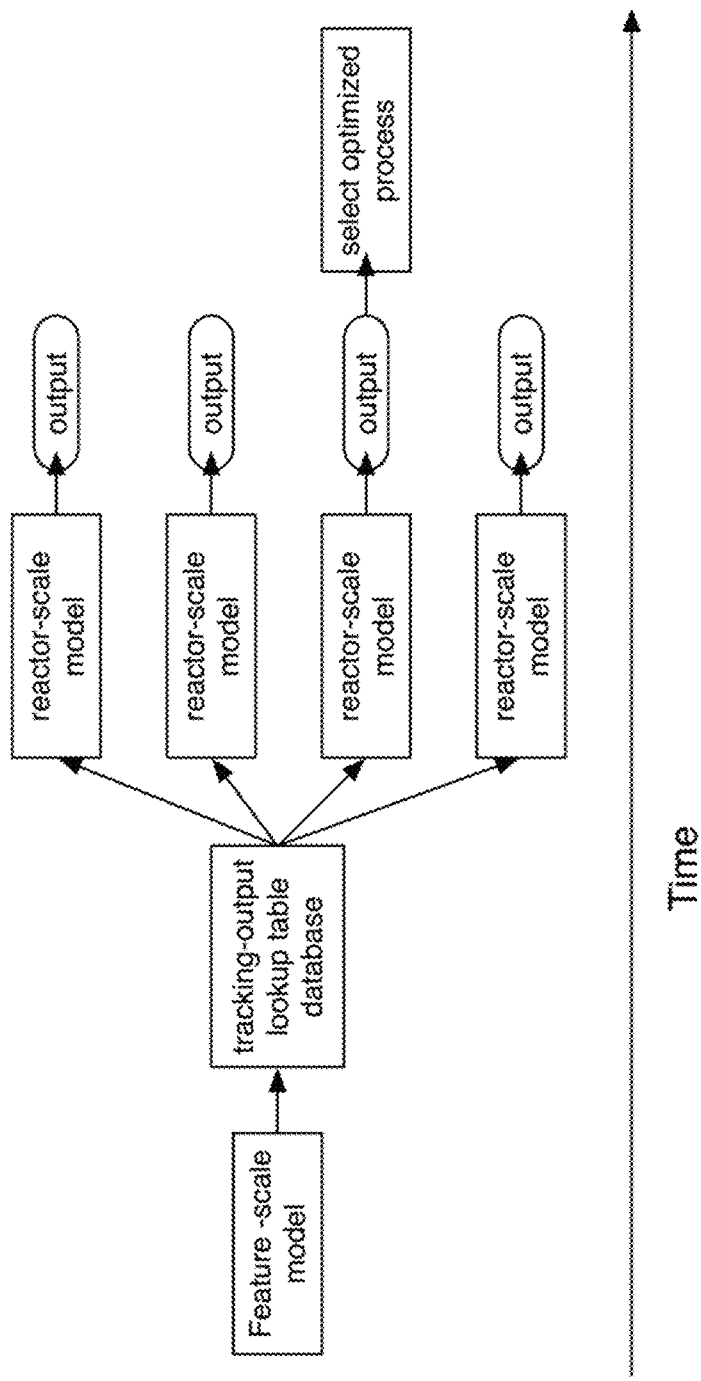
FIG. 16 illustrates concurrent solution of coating of nanostructured materials to optimize the materials synthesis process

The systems and methods of the present invention can be utilized in numerous applications. FIG. 11 illustrates a simulation domain for the coating of a 6×6 in nanostructured material in a cross-flow ALD reactor. FIG. 12 the initial sticking probability values both inside and outside of the nanostructured material for said simulation. FIG. 13 illustrates a simulation of the coating of a 6×6 inch high surface area material in a cross-flow reactor using the method described in the invention: in this case, the final sticking probability is not homogeneous as a consequence of the large surface area material being inhomogeneously coated. FIG. 14 illustrates the effect of the presence of a high surface area material on the precursor pressure at a reactor scale: precursor pressure mid height of the deposition reactor after 1 s, showing how precursor depletion is responsible for the spatial inhomogeneities. FIG. 15 illustrates an application example of the invention: precursor depletion due to the coating of a nanostructure material in a roll-to-roll set up. FIG. 16 illustrates a concurrent solution of coating of nanostructured materials to optimize the materials synthesis process. FIG. 13 and FIG. 14 highlight the close link between reactor-scale flow patterns and the coating of the nanostructured material. Using the method described above, this coupling is achieved without having to solve the reactor and feature scale concurrently. Instead, the process described in FIG. 16 was applied to the solution of this particular problem.

Figure 10:
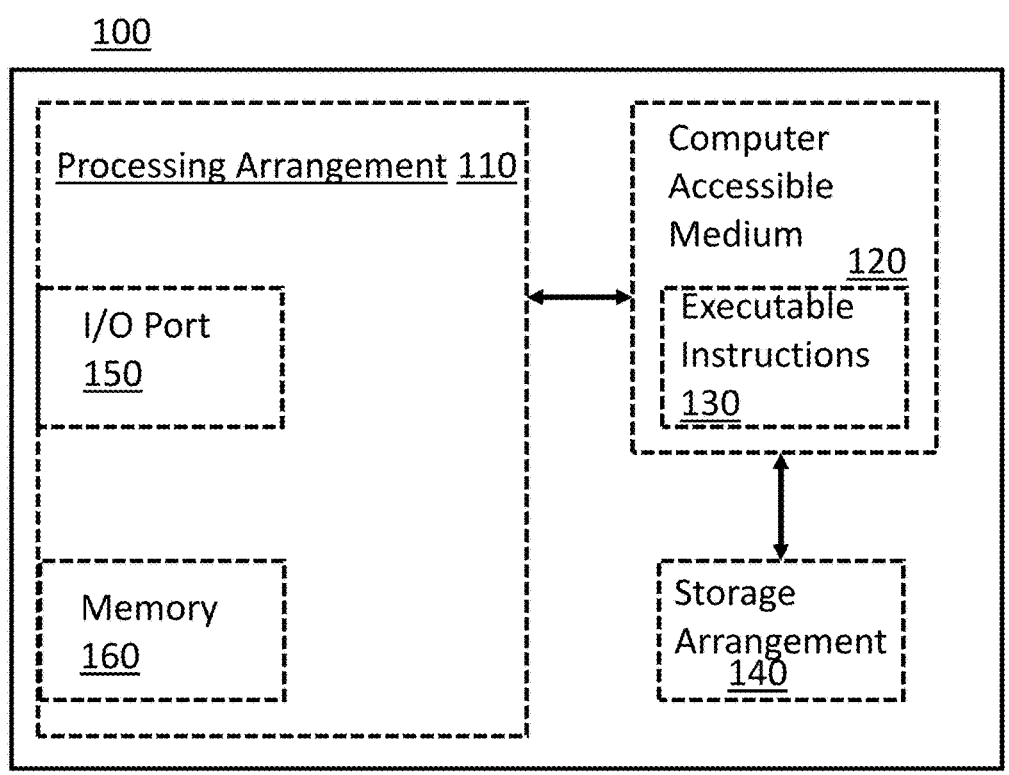
FIG. 10 illustrates a computer system for use with certain implementations.

As shown in FIG. 10, e.g., a computer-accessible medium 120 (e.g., as described herein, a storage device such as a hard disk, floppy disk, memory stick, CD-ROM, RAM, ROM, etc., or a collection thereof) can be provided (e.g., in communication with the processing arrangement 110). The computer-accessible medium 120 may be a non-transitory computer-accessible medium. The computer-accessible medium 120 can contain executable instructions 130 thereon. In addition or alternatively, a storage arrangement 140 can be provided separately from the computer-accessible medium 120, which can provide the instructions to the processing arrangement 110 so as to configure the processing arrangement to execute certain exemplary procedures, processes and methods, as described herein, for example. The instructions may include a plurality of sets of instructions. For example, in some implementations, the instructions may include instructions for applying radio frequency energy in a plurality of sequence blocks to a volume, where each of the sequence blocks includes at least a first stage. The instructions may further include instructions for repeating the first stage successively until magnetization at a beginning of each of the sequence blocks is stable, instructions for concatenating a plurality of imaging segments, which correspond to the plurality of sequence blocks, into a single continuous imaging segment, and instructions for encoding at least one relaxation parameter into the single continuous imaging segment.

System 100 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. Therefore, the above embodiments should not be taken as limiting the scope of the invention.

What is claimed is:

1. A method for modeling to model reaction and transport of gases and liquid comprising:
   identifying a set of tracking variables that completely define the state of the nanostructured material;
   identifying a set of output variables that completely define the impact of the nanostructured substrate at the reactor scale;
   computing, via a processor of a computer, the set of output variables as a function of the set of tracking variables to generate a functional relationship between the set of tracking variables and the set of output variables;
   storing the functional relationship between the tracking and the output variables both as a data structure in a memory of the computer;

solving the reactive transport at a reactor scale of the reacting species and the tracking variables using an iterative method; and determining, via the processor, the value of the output variables from the tracking variables using the functional relationship between them stored in the memory for every discretized region of the reactor-scale model interacting with the nanostructured material and for all iteration steps.

2. The method of claim 1, where the data structure is a structure selected from the group consisting of a lookup table, a hash or dictionary, a tree structure, and a relational database.

3. The method of claim 1, further comprising determining at runtime whether the output variables can be determined by direct lookup or requires solving a feature scale model.

4. The method of claim 1, further comprising compiling a database storing the functional relationship between tracking and output variables that can be used by multiple simulations without having to recompute the feature-scale model.

5. The method of claim 1, further comprising applying a computational fluid dynamic model for solving the reactive transport at the reactive scale of the reacting species and the tracking variables.

6. The method of claim 1, wherein the set of output variables is given by the effective sticking probability for each of the reactive molecules being solved at the reactor-scale.

7. The method of claim 1, wherein the feature-scale model comprises:
defining a set of transient states corresponding to the reversible interaction of reacting molecules with the surface of the nanostructured materials and defining a set of absorbing states corresponding to the final outcome of the process of either a molecule reacting with the feature or escaping from the surface;
defining a set of transition probabilities between transient states and between transient and absorbing states;
solving the probabilistic outcome using absorbing Markov Chain formalism.

8. A method for simulating reactor-scale ALD, comprising generating a look-up table for feature-scale values;
applying a feature-scale model having a plurality of time-steps;
for each of the plurality of time steps, identifying a plurality of surface element;
for each plurality of surface elements corresponding to each of the plurality of time steps, determining a total precursor exposure and querying the look-up table based upon the determined total precursor exposure to determine a reaction probability; and
applying the reaction probability at the reactor-scale.

9. The method of claim 8, wherein the connection between the feature and reactor scale models takes place using the method derived in claim 1.

10. The method of claim 9, wherein generating the look-up table comprises:
determining nanostructures for the thin film deposition;
modeling transport of a reacting molecule in the thin film deposition as a Markov chain process;
determining a probability that a reacting molecule adsorbs.

11. A computer implemented system for simulating reactor-scale ALD, comprising:
a processor,
non-transitory computer-readable memory having instructions thereon, the instructions for:
determining nanostructures for the thin film deposition;
modeling transport of a reacting molecule in the thin film deposition as a Markov chain process;
determining a probability that a reacting molecule adsorbs; and
applying the probably to a reactor-scale to simulate a thin film deposition on a reactor scale.

12. The computer implemented system of claim 11, wherein modeling transport includes a plurality of transition states corresponding to adsorption and recombination.

13. A method to allow the concurrent solution of the coating of nanostructured materials consisting of:
solving a feature-scale model to determine look-up tables for the relevant tracking and output variables for the nanostructured material;
storing the results in a database for future retrieval; and
concurrently solving the reactor-scale model for a multiplicity of conditions and reactor configurations.

14. The method in claim 13 further comprising optimizing the processing conditions in a physical reactor.

15. The method in claim 14 further comprising optimizing the design of a physical reactor.

16. The method of claim 13 further comprising optimizing design of core-shell structure materials.

17. The method of claim 16, wherein the core-shell structure materials are selected from the group consisting of core-shell nanostructured electrodes, core-shell particles, and the conformal coating with multilayers of high aspect ratio features and recessed substrates.

* * * * *